United States Patent [19]

Kiser

[11] Patent Number: 4,868,346

[45] Date of Patent: Sep. 19, 1989

[54] REMOVAL OF WATER FROM AQUEOUS ALCOHOL MIXTURES

[75] Inventor: Donald L. Kiser, Muscatine, Iowa

[73] Assignee: Grain Processing Corporation, Muscatine, Iowa

[21] Appl. No.: 794,666

[22] Filed: Nov. 4, 1985

[51] Int. Cl.$^4$ .................. C07C 29/76; C07C 31/08
[52] U.S. Cl. ........................................ 568/916
[58] Field of Search ........................................ 568/916

[56] References Cited

U.S. PATENT DOCUMENTS

| | | | |
|---|---|---|---|
| 3,132,079 | 5/1964 | Epperly et al. | 202/67 |
| 3,691,728 | 9/1972 | Vautrain et al. | 55/33 |
| 4,319,057 | 3/1982 | Kiser | 568/916 |
| 4,333,740 | 6/1982 | Priegnitz | 568/916 |
| 4,345,973 | 8/1982 | Ladisch et al. | 568/916 |
| 4,351,732 | 9/1982 | Psaras et al. | 568/916 |
| 4,359,592 | 11/1982 | Chao et al. | 568/916 |
| 4,469,805 | 9/1984 | Kofke et al. | 502/33 |

FOREIGN PATENT DOCUMENTS 240694 4/1969 U.S.S.R. .............................. 568/916

OTHER PUBLICATIONS

Bushuk et al, "Cer. Chem.", (1957), pp. 87–93.
Hong et al, "Biotechnology and Bioengineering", vol. XXIV, (1982) pp. 725–730.
Ladisch et al, "Ind. Eng. Chem. Process Der. Dev." (1984)23, pp. 437–443.
Ladisch et al, "Science", vol. 205 (1979), pp. 898–900.
Sair et al, "I. & E.C.", vol. 36 (1944) pp. 316–319.

*Primary Examiner*—J. E. Evans
*Attorney, Agent, or Firm*—Neuman, Williams, Anderson & Olson

[57] ABSTRACT

Process for removing water from mixtures of alcohols and water by contacting such a mixture with a substantially dehydrated solid absorbent which comprises particulate starch-containing vegetable matter such as corn starch, potato starch, cracked corn, corn hulls, grains such as barley, wheat, rye, sorghum, oats, milo and the like.

9 Claims, No Drawings

REMOVAL OF WATER FROM AQUEOUS ALCOHOL MIXTURES

This invention relates to methods for removing water from alcohols.

For use in certain applications alcohols must be substantially free of water. For example, anhydrous ethanol is used as an automotive fuel by itself or, more usually, as a gasohol blend with gasoline. For such uses, it is desired that the alcohol be anhydrous, i.e., substantially free of water.

Ethanol is commonly produced from corn by fermentation processes to produce an aqueous mixture containing at most about 12% ethanol. Distillation can then increase the alcohol content to about 95% and to further increase the alcohol content azeotropic distillation using a third component, such as an organic solvent is commonly employed. Azeotropic distillation is costly and for this and other reasons prior art workers have directed attention to other methods for dehydrating alcohols.

U.S. Pat. No. 4,345,973 discloses a procedure for dehydration of aqueous ethanol which involves heating an aqueous ethanol solution to the vapor state and then allowing the vapor to contact a dehydrating agent, such as corn starch or corn hulls, that had previously been stripped of water by heating. This procedure, like the azeotropic distillation processes, depends on vapor dehydration reactions. According to the patented process, the water absorbing material must first be prepared for use by heating. This again requires considerable energy input. The characteristics of the absorbents which cause water to be removed from the ethanol-water mixtures also result in the extracted water being strongly held or bound by the absorbents. Thus, to prepare the dehydration agents for use according to the '973 patent, energy far beyond that required to merely bring the absorbent mass to the vaporization temperature of water is required if removal of water therefrom is to be accomplished in a reasonable time.

The procedure of the '973 patent depends on contact of vapor with a solid and thus is a vapor dehydration procedure. Since small quantities of liquid occupy a large volume in the vapor state, the vapor dehydration procedure involves high energy costs to accomplish and maintain the materials in vapor state and also presents problems of achieving efficient contact of the vapor with the absorption agent. Thus, one practicing the patented vapor dehydration procedure must slow the passage of vapor through the absorbent to allow adequate contact time or be satisfied with only partial dehydration or utilize sufficient capital intensive equipment to handle large vapor volumes.

Similarly, U.S. Pat. No. 4,333,740 relates to a process for the separation of water from ethanol. According to this patent, corn meal is used to absorb the water present with the ethanol. To make the corn meal suitable for use it is heated with 50° C. to 60° C. air to dryness. According to the patent, the corn meal exhibits a capacity to absorb only about 0.0225 gram water per gram of dry corn meal.

Both of the above prior art patents require that the absorption agent be heated and dried before use to remove water from ethanol. Further, such dried or dehydrated vegetable materials having high surface area, such as starch, present explosion hazards and extreme care must be exercised in transporting and using such dehydrated solids. The explosion hazards constitute serious drawbacks with respect to the above prior art methods of removing water from alcohols.

It is therefore a principal object of this invention to provide methods for removing water from mixtures of alcohol and water which possess advantages over prior art methods.

Another object of this invention is to provide improved methods for removing water from alcohol-water mixtures which can be conducted in liquid state below the vaporization temperature of the alcohols.

An additional object of the invention is to provide processes for removing water from water-alcohol mixtures utilizing readily available absorbents which can be used for more than one absorption cycle without moving the absorbents from one vessel to another between cycles and without applying heat to the absorbents between cycles.

The present invention involves a process for removing water from mixtures of alcohols and water by contacting such a mixture with a substantially dehydrated solid absorbent which comprises particulate starch-containing vegetable matter such as corn starch, potato starch, cracked corn, corn hulls, grains such as barley, wheat, rye, sorghum, oats, milo and the like. Prior to use for dehydration, the absorbent itself is dehydrated by contacting it with methanol, acetone or other low molecular weight hydrophilic solvent.

The process of the present invention comprises contacting a particulate vegetable absorbent containing starch with methanol or acetone in liquid state to remove water therefrom and to produce a substantially anhydrous absorbent and then contacting the substantially anhydrous absorbent with an aqueous alcohol mixture to remove water therefrom.

The dehydration procedure can be conducted in either a batch or continuous manner. For example, in a typical batch dehydration procedure, the selected solid vegetable absorbent is placed into a vessel and methanol or acetone preferably containing not more than 0.1% by weight water is brought into contact therewith. The amount of methanol or acetone used generally ranges from about at least 3 to 30 milliliters for each gram of the absorbent. A large ratio of methanol or acetone to the absorbent, such as 10 or more to 1, milliliters per gram, is generally preferred to desorb the maximum amount of water. Occasional stirring or other agitation is desirable to improve efficiency. The methanol or acetone is permitted to remain in contact with the absorbent for periods of from about 1 to 8 hours. The extent of water desorbed from the absorbent increases with extended contact times but with decreasing efficiency. After contact with the methanol or acetone for a desired period so that the absorbent is substantially free of water, i.e. contains not more than about 4% water, the bulk of the methanol or acetone is removed from the absorbent by gravity drainage or by application of a vacuum thereto. If desired or necessary, residual methanol or acetone can be removed from the dehydrated absorbent by purging the absorbent mass with an inert gas such as air or nitrogen. However, in cases where carryover in the final product of some residual methanol or acetone is not objectionable, the gas purge is not necessary. For example, minor amounts of methanol or acetone are not objectionable in ethanol to be used in motor fuels. In any event, the treated dehydrated absorbent is then ready for use to remove water from alcohol-water mixtures. This is accomplished by contacting the prepared absorbent with the aqueous alcohol solution in liquid state whereby the water is selectively removed from the alcohol.

In a typical continuous dehydration operation, a selected absorbent is packed into a vessel, such as an elongated column, equipped with a bottom distributor plate and inlet and outlet openings at the bottom and top, respectively. Then methanol or acetone is made to flow through the bed by perculating or pumping until the absorbent bed is substantially dehydrated, i.e., the absorbent contains less than about 1% water. At this point, the column can be purged with a gas if desired or can be immediately used to remove water from an aqueous alcohol. The dehydration efficiency is a function of the flow rate of the aqueous alcohol solution undergoing dehydration. A relatively slow flow rate increases the contact time of the solution with the absorbent mass and affords greater moisture removal per absorbent unit. A flow rate which provides a contact time of from 3 to 30 minutes between the aqueous alcohol solution and the absorbent is generally preferred. The effluent exiting from the column can be monitored for water content to determine when the dehydration efficiency of the column has decreased below a desired level. When the efficiency of dehydration has fallen below a predetermined level, introduction of the aqueous alcohol solution is stopped. The column can then be regenerated by passing methanol or acetone therethrough. The dehydration and regeneration cycles can be alternately repeated.

The absorption column can be of any suitable dimensions that provide efficient flow of liquid past a solid absorbent, but a ratio of diameter:length in the range 1:5 to 1:40 is preferred. A frit or mesh on the discharge end is used to keep packing in the column during the elution cycles. The ends of the column have suitable fittings attached to permit pumping of liquids through the column and, if appropriate, to attach a purge gas inlet.

The direction of flow through the column is not critical to achieving the desired results. Upflow more efficiently removes air entrapped during packing. The column can be operated over a range of temperatures, from subambient up to a temperature slightly below the vaporization temperature of the alcohol undergoing dehydration.

The vegetable absorbent materials are employed according to this invention in a divided or particulate form. Generally, the particle size of the absorbent will preferably fall within the range of 0.01 to 1 millimeter.

The dehydration methods of the present invention can be advantageously employed to remove water from mixtures of water and alcohols, such as ethanol, 1-propanol and 2-propanol, and other aqueous mixtures, such as moist non-polar organic compositions such as petroleum fluids.

The following examples illustrate the invention and the advantages thereof.

EXAMPLE 1

A 1.1×46 centimeter column was filled with 30 grams corn starch which had been equilibrated at moderate humidity and contained 9.2% water. This column was jacketed so that the column contents could be held at 60° C. Ethanol containing 5.54% water weight/volume was passed through the column at a rate of approximately 0.53 milliliters per minute. The first 5 milliliters of the aqueous ethanol solution removed from the column (effluent) contained 6.32% water weight/volume; the next 5 milliliters of effluent contained 11.91% water and the third 5 milliliters of effluent contained 9.92% water.

The experiment indicated that the hydrated corn starch does not dehydrate the aqueous ethanol, even at a temperature of 60° C.

EXAMPLE 2

A 1.1×46 centimeter column was filled with 32.0 grams of corn starch containing 9.2% water, as determined by forced-air oven assay. The column was jacketed and held at 60° C. Substantially anhydrous methanol containing 0.056% water, was pumped through the column at a rate of 0.60 milliliters per minute. The first 5 milliliters of methanol removed from the column (effluent) contained 1.37 grams water; the next 5 milliliters of effluent contained an additional 0.88 gram water. A total of 2.99 grams of water was removed by passing 30 milliliters of methanol through the column.

Nitrogen was slowly passed through the column for a few minutes to purge methanol. Then an aqueous ethanol solution containing 6.04% water weight/volume was pumped through the dehydrated starch column. The first 5 milliliters of effluent contained 96% methanol; the next 5 milliliters of effluent contained about 71% ethanol, 29% methanol and only 0.32% water; the next 5 milliliters of effluent contained about 95% ethanol, 5% methanol and 0.34% water; the next 5 milliliters of effluent contained 98% ethanol, 2% methanol and 0.25% water; and the next 10 milliliters of effluent contained 0.27% water and no methanol and was predominantly ethanol.

This data demonstrates that aqueous ethanol can be dehydrated in the liquid state by passing the moist alcohol through a column of starch previously dehydrated with methanol.

The starch remaining in the column is a high quality starch useful in applications calling for high purity starch or for fermentation in alcohol production or for additional dehydration cycles.

EXAMPLE 3

An additional 30 milliliters of ethanol containing 6.04% water was passed through the column of starch used in Example 2. The effluent was monitored for moisture as the ethanol passed through the column. The last 10 milliliters of effluent contained 5.90% water indicating that the previously dehydrated starch column was again nearly saturated with water.

Ethanol flow to the column was then stopped and nitrogen used to purge excess ethanol from the column. Next methanol was again pumped through the column, as was done in Example 2. The first 10 milliliter aliquot of effluent contained 9.91% water and 14% ethanol and the second 10 milliliters of effluent contained 5.03% water and no ethanol. Thus, the first 20 milliliters of effluent contained 1.49 grams water while the next 80 milliliters of effluent contained 0.25 grams water.

As in Example 2, excess methanol was removed from the dehydrated starch with nitrogen purge, then aqueous ethanol pumped through th column. The ethanol, containing 5.62% water, was pumped to the column at a rate of 0.61 milliliters per minute. The first 10 milliliters of effluent contained 0.22% water and 8.8% methanol, the next 10 milliliters contained 0.23% water and 2.0% methanol. The first 30 milliliters collected contained 0.43% water.

This example illustrates that more than one dehydration cycle can be conducted.

EXAMPLE 4

A column was packed with 21.75 grams corn starch containing 9.6% water. The column for this example was not heated, being operated at ambient temperature of about 25° C. Methanol containing 0.016% water was pumped through the column at a rate of 0.35 milliliters per minute. The first 5 milliliter aliquot of effluent contained 24.5% water and thus removed 1.22 grams water from the starch. The first 15 milliliters of methanol passed through the column removed 1.85 grams water. Forty additional milliliters of methanol was put through the column. A total of 1.96 grams water was removed from the starch during the passage of 55 milliliters of methanol therethrough.

Excess methanol was then removed from the column with a slow air purge. Next, with the column still at 25° C., aqueous ethanol containing 5.05% water was pumped through the column at a rate of 0.43 milliliter per minute. The first 10 milliliters of effluent contained essentially methanol. The next two 5 milliliter cuts contained, respectively, 23% methanol, 0.08% water and 3% methanol and 0.07% water. The next 5 milliliters of effluent was essentially ethanol, containing 0.09% water and no detectable methanol. Ethanol in the next 10 milliliters was less completely dehydrated, containing 3.21% water.

EXAMPLE 5

Approximately 24.5 grams cracked corn, medium grind (particle size about 2 millimeters) containing 11.7% water was placed in a column. Methanol containing 0.13% water was pumped through the column at room temperature. The first 5 milliliter aliquot of effluent contained 15.6% water and the second 5 milliliters of effluent contained 5.2% water. A total volume of 50 milliliters of methanol passed through the column removed 1.37 grams water.

The column was then purged with air for 30 minutes, following which aqueous ethanol containing 5.83% water was pumped through the column, at room temperature, at a rate of 0.23 milliliters per minute. The first 5 milliliters of effluent contained 99% methanol, the next 5 milliliters 69%. The next three 5 milliliter aliquots of effluent contained 32%, 13% and 5.6% methanol, respectively. Moisture in these three cuts was 0.66%, 1.08% and 2.12%, respectively. 0.048 gram water was removed from the ethanol solution for each gram of dry corn meal. In a later experiment conducted as above, methanol-treated finely ground cracked corn removed 0.087 gram of water per gram of corn.

EXAMPLE 6

An absorbent consisting of 18.2 grams corn hulls containing 1.27 grams water was placed in a 1.1×46 centimeter column. Methanol was pumped through the column at room temperature. The first 15 milliliters of effluent removed 0.88 gram water; the next 155 milliliters methanol removed an additional 0.31 gram water.

The column was next heated to 80° C. and purged with a gentle flow of air to remove the major portion of residual methanol. The column was than cooled and ethanol containing 4.77% water pumped through. The first 5 milliliters of effluent ethanol contained only 5% methanol and no detectable moisture. The next 5 milliliters of effluent contained 4% methanol and 0.38% water.

This data shows that heating of methanol-treated absorbent can aid in minimizing methanol carryover into dehydrated ethanol.

After sufficiently desired usage for removal of water in accordance with this invention, the starch-containing absorbents can, if desired, be used for production of alcohol by fermentation.

Those modifications and equivalents which fall within the spirit of the invention are to be considered a part thereof.

What is claimed is:

1. A process for the removal of water from aqueous alcohol mixtures which comprises:
   contacting a starch-containing particulate vegetable absorbent with methanol or acetone in liquid state to remove water therefrom and to produce a substantially anhydrous absorbent and then contacting the substantially anhydrous absorbent with an aqueous alcohol mixture to remove water therefrom.

2. A process in accordance with claim 1 wherein the aqueous alcohol is an aqueous ethanol mixture.

3. A process in accordance with claim 1 wherein the starch-containing particulate vegetable absorbent is a starch-containing grain.

4. A process in accordance with claim 1 wherein the starch-containing particulate vegetable absorbent is corn starch.

5. A process in accordance with claim 1 wherein the starch-containing particulate vegetable absorbent is cracked corn.

6. A process in accordance with claim 1 wherein the starch-containing particulate vegetable absorbent is corn hulls.

7. A process for removing water from aqueous alcohol mixtures which comprises passing methanol or acetone through a bed of a starch-containing particulate vegetable absorbent in liquid state to remove water therefrom and to produce a substantially anhydrous absorbent, then passing through the bed of substantially anhydrous absorbent an aqueous alcohol mixture to remove water therefrom and then again passing methanol or acetone through said bed.

8. A process in accordance with claim 1 wherein the substantially anhydrous absorbent is contacted with an aqueous alcohol mixture in liquid state.

9. A process in accordance with claim 7 wherein the aqueous alcohol mixture which is passed through the bed of substantially anhydrous absorbent is in liquid state.

* * * * *